(12) United States Patent
Chason et al.

(10) Patent No.: US 9,795,141 B2
(45) Date of Patent: Oct. 24, 2017

(54) ANTIMICROBIAL POLYMER SYSTEMS USING MULTIFUNCTIONAL ORGANOMETALLIC ADDITIVES FOR POLYURETHANE HOSTS

(71) Applicant: DMR INTERNATIONAL, INC., Woodstock, IL (US)

(72) Inventors: Marc Chason, Schaumburg, IL (US); Daniel Roman Gamota, Palatine, IL (US); Rick Latella, Woodstock, IL (US)

(73) Assignee: DMR International, Inc., Woodstock, IL (US)

( * ) Notice: Subject to any disclaimer, the term of this patent is extended or adjusted under 35 U.S.C. 154(b) by 426 days.

(21) Appl. No.: 13/833,445

(22) Filed: Mar. 15, 2013

(65) Prior Publication Data

US 2014/0199356 A1    Jul. 17, 2014

Related U.S. Application Data

(60) Provisional application No. 61/751,940, filed on Jan. 14, 2013.

(51) Int. Cl.
| | | |
|---|---|---|
| A01N 55/02 | (2006.01) | |
| A01N 37/02 | (2006.01) | |
| A01N 59/16 | (2006.01) | |
| A01N 59/20 | (2006.01) | |

(52) U.S. Cl.
CPC ............ *A01N 55/02* (2013.01); *A01N 37/02* (2013.01); *A01N 59/16* (2013.01); *A01N 59/20* (2013.01)

(58) Field of Classification Search
None
See application file for complete search history.

(56) References Cited

U.S. PATENT DOCUMENTS

| | | | |
|---|---|---|---|
| 3,590,000 | A | 6/1971 | Palermiti |
| 3,983,185 | A | 9/1976 | Dorfman et al. |
| 4,428,989 | A | 1/1984 | Marshall |
| 5,227,093 | A | 7/1993 | Cole et al. |
| 5,300,249 | A | 4/1994 | Schwartz et al. |
| 5,439,957 | A | 8/1995 | Takimoto et al. |
| 6,113,979 | A | 9/2000 | Sagawa et al. |
| 7,022,750 | B2 | 4/2006 | Camp et al. |
| 7,354,596 | B1 * | 4/2008 | Banovetz et al. ............ 424/408 |
| 7,595,355 | B2 | 9/2009 | Trogolo |
| 7,998,498 | B2 | 8/2011 | Szycher |
| 8,124,169 | B2 | 2/2012 | Ylitalo et al. |
| 2006/0188551 | A1 | 8/2006 | Hauser et al. |
| 2008/0051493 | A1 | 2/2008 | Trogolo et al. |
| 2008/0207774 | A1 | 8/2008 | Krishnan |
| 2008/0226584 | A1 | 9/2008 | Krishnan |
| 2008/0269186 | A1 | 10/2008 | Bignozzi et al. |
| 2008/0317800 | A1 | 12/2008 | Amirzadeh-Asl |
| 2009/0093577 | A1 | 4/2009 | Bernard et al. |
| 2009/0130157 | A1 | 5/2009 | Ylitalo et al. |
| 2000/9186064 | | 7/2009 | Szycher |
| 2009/0186064 | A1 * | 7/2009 | Szycher ....................... 424/423 |
| 2009/0201759 | A1 | 8/2009 | Mills |
| 2010/0204357 | A1 | 8/2010 | Chasser et al. |
| 2010/0330142 | A1 | 12/2010 | Falk et al. |
| 2011/0002872 | A1 | 1/2011 | Ohashi et al. |
| 2012/0015009 | A9 | 1/2012 | Taylor et al. |
| 2012/0272967 | A1 | 11/2012 | Stewart et al. |

FOREIGN PATENT DOCUMENTS

| | | |
|---|---|---|
| EP | 0290095 A1 | 11/1988 |
| GB | 709575 | 10/1951 |
| JP | 2008222564 A | 9/2008 |
| WO | 01/32138 A1 | 5/2001 |
| WO | 2005061022 A2 | 7/2005 |
| WO | 2012091407 A2 | 7/2012 |
| WO | 2012158702 A2 | 11/2012 |

OTHER PUBLICATIONS http://www.merriam-webster.com/dictionary/disperse.*
International Search Report dated Apr. 25, 2014 in corresponding International Patent Application No. PCT/IB2014/058130.
International Search Report dated May 19, 2014 in corresponding International Patent Application No. PCT/IB2014/058127.
International Search Report dated Oct. 28, 2013 in related International App. No. PCT/IB/2013/054604.
Office Action received in U.S. Appl. No. 13/833,689 mailed Jun. 5, 2014.
Office Action received in U.S. Appl. No. 13/833,445 mailed Jul. 7, 2014.
Office Action received in U.S. Appl. No. 13/833,689 mailed Aug. 19, 2014.
Office Action received in U.S. Appl. No. 13/833,581 mailed Sep. 3, 2014.
Office Action received in U.S. Appl. No. 13/833,581 mailed May 13, 2015.
Office Action received in U.S. Appl. No. 13/833,581 mailed Dec. 10, 2014.
Office Action mailed Dec. 30, 2016 in corresponding U.S. Appl. No. 14/277,112.
Office Action mailed Sep. 12, 2016 in corresponding U.S. Appl. No. 13/833,581.

* cited by examiner

*Primary Examiner* — Robert A Wax
*Assistant Examiner* — Danah Al-Awadi
(74) *Attorney, Agent, or Firm* — Miles & Stockbridge P.C.; Ajay A. Jagtiani

(57) ABSTRACT

Described are antimicrobial polymer products made from mixtures of antimicrobial organometallic additives dispersed throughout a polymer host matrix.

20 Claims, 7 Drawing Sheets

ANTIMICROBIAL POLYMER SYSTEMS USING MULTIFUNCTIONAL ORGANOMETALLIC ADDITIVES FOR POLYURETHANE HOSTS

CROSS-REFERENCE TO RELATED APPLICATIONS

This application claims benefit of priority to U.S. Provisional Patent Application No. 61/751,940 to Chason et al., entitled "ANTI-MICROBIAL POLYMER SYSTEMS USING MULTIFUNCTIONAL ORGANOMETALLIC ADDITIVES," filed Jan. 14, 2013 which is incorporated herein by reference in its entirety.

BACKGROUND

Field of the Invention

The present invention relates to antimicrobial polymer systems.

Related Art

Material surfaces of polymer products may become contaminated with disease-causing agents. For example, used in aqueous environments or environments where moisture is present, microbes may be transferred to the surface of the polymer products.

SUMMARY

According to a first broad aspect, the present invention provides a product comprising: a polymer host matrix comprising polyurethane, and one or more antimicrobial organometallic additives dispersed throughout the polymer host matrix, wherein each of the one or more antimicrobial organometallic additives is water insoluble or sparingly soluble in water and comprises a long-chain fatty acid group, and wherein a majority of metallic species dispersed throughout the polymer host matrix are in the one or more antimicrobial organometallic additives.

According to a second broad aspect, the present invention provides a method comprising the following step: (a) mixing one or more antimicrobial organometallic additives with a liquid polyurethane at room temperature to form a polymer product comprising the one or more antimicrobial organometallic additives dispersed throughout the polymer host matrix, wherein each of the one or more antimicrobial organometallic additives is water insoluble or sparingly soluble in water and comprises a long-chain fatty acid group, wherein a majority of metallic species dispersed throughout the polymer host matrix are in the one or more antimicrobial organometallic additives.

According to a third broad aspect, the present invention provides a product comprising: a polymer host matrix comprising polyurethane, and one or more antimicrobial organometallic additives dispersed throughout the polymer host matrix, wherein the one or more antimicrobial organometallic additives comprise a mixture of two or more members of the group consisting of the following antimicrobial organometallic additives: silver stearate, cupric stearate and zinc stearate.

According to a fourth broad aspect, the present invention provides a product comprising: a substrate, and a thermoset powder coating on the substrate, wherein the thermoset powder coating comprises a polymer host matrix and one or more antimicrobial organometallic additives dispersed throughout the polymer host matrix, wherein each of the one or more antimicrobial organometallic additives is water insoluble or sparingly soluble in water and comprises a long-chain fatty acid group, and wherein a majority of the metallic species dispersed throughout the polymer host matrix are in the one or more antimicrobial organometallic additives.

According to a fifth broad aspect, the present invention provides a method comprising the following step: (a) heating a mixture on a substrate to melt the mixture to form a thermoset powder coating on the substrate, wherein the mixture comprises one or more antimicrobial organometallic powders mixed with a thermosetting powder, wherein the thermoset powder coating comprises a polymer host matrix and one or more antimicrobial organometallic additives dispersed throughout the polymer host matrix, wherein each of the one or more antimicrobial organometallic additives is water insoluble or sparingly soluble in water and comprises a long-chain fatty acid group, and wherein a majority of the metallic species dispersed throughout the polymer host matrix are in the one or more antimicrobial organometallic additives.

According to a sixth broad aspect, the present invention provides a product comprising: a substrate, and a thermoset powder coating on the substrate, wherein the thermoset powder coating comprises a polymer host matrix and one or more antimicrobial organometallic additives dispersed throughout the polymer host matrix, and wherein the one or more antimicrobial organometallic additives comprise a mixture of two or more members of the group consisting of the following antimicrobial organometallic additives: silver stearate, cupric stearate and zinc stearate.

According to a seventh broad aspect, the present invention provides a product comprising: a polymer host matrix comprising paraffin wax, and one or more antimicrobial organometallic additives dispersed throughout the polymer host matrix, wherein each of the one or more antimicrobial organometallic additives is water insoluble or sparingly soluble in water and comprises a long-chain fatty acid group, and wherein a majority of metallic species dispersed throughout the polymer host matrix are in the one or more antimicrobial organometallic additives.

According to an eighth broad aspect, the present invention provides a method comprising the following step: (a) mixing one or more antimicrobial organometallic additives with liquid paraffin wax to form a polymer product comprising the one or more antimicrobial organometallic additives dispersed throughout the polymer host matrix, wherein each of the one or more antimicrobial organometallic additives is water insoluble or sparingly soluble in water and comprises a long-chain fatty acid group, wherein a majority of metallic species dispersed throughout the polymer host matrix are in the one or more antimicrobial organometallic additives.

According to a ninth broad aspect, the present invention provides a product comprising: a polymer host matrix comprising paraffin wax, and one or more antimicrobial organometallic additives dispersed throughout the polymer host matrix, wherein each of the one or more antimicrobial organometallic additives is water insoluble or sparingly soluble in water and comprises a long-chain fatty acid group, and wherein the one or more antimicrobial organometallic additives comprise a mixture of two or more members of the group consisting of the following antimicrobial organometallic additives: silver stearate, cupric stearate and zinc stearate.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention. The sizes and the relative heights, widths, diameters, thicknesses, etc. of features in the drawings are not necessarily to scale unless specifically indicated otherwise. For example, in the drawings the thickness of a coating in the drawings may be shown thicker relative to the substrate on which the coating is coated to allow for details of the components of the coating to be better illustrated. Also in the drawings, organometallic additives are shown as being much larger than these components would be in the polymer host matrix in which these components are dispersed for ease of illustration. In the drawings, the organometallic additives are depicted as circles. This is only a schematic representation as the additive form factor of the present invention may be circular, spherical, linear, branched or other form factor.

DETAILED DESCRIPTION OF THE PREFERRED EMBODIMENTS

Definitions

Figure 1:
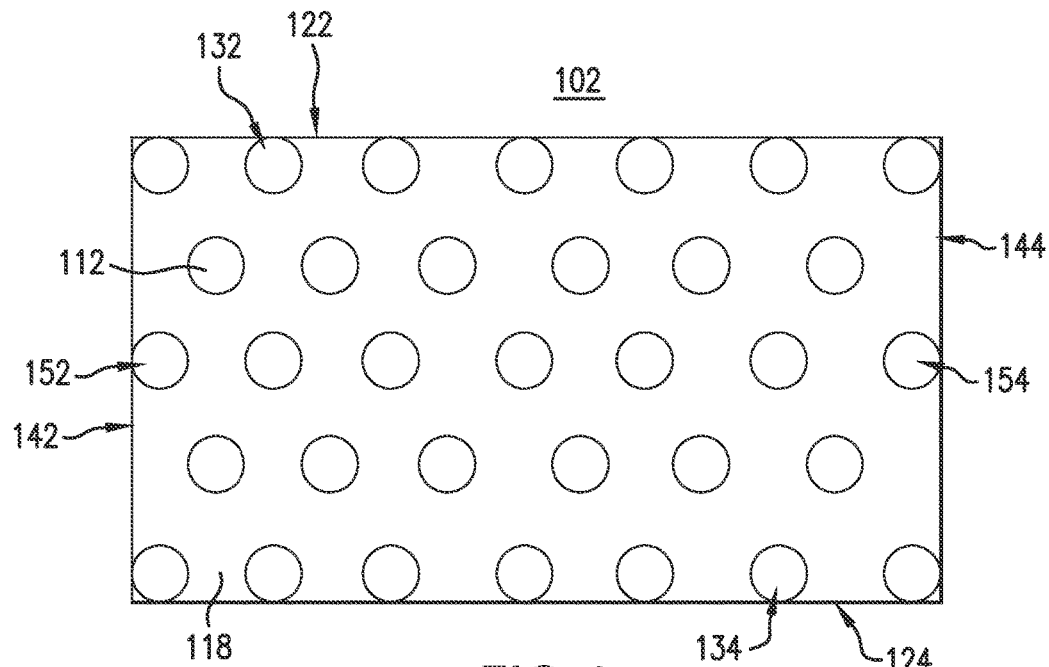
FIG. 1 is a schematic drawing of a polymer product having dispersed therein an organometallic additive according to one embodiment of the present invention.

Where the definition of terms departs from the commonly used meaning of the term, applicant intends to utilize the definitions provided below, unless specifically indicated.

For purposes of the present invention, it should be noted that the singular forms, "a," "an," and "the" include reference to the plural unless the context as herein presented clearly indicates otherwise.

For purposes of the present invention, directional terms such as "top," "bottom," "upper," "lower," "above," "below," "left," "right," "horizontal," "vertical," "up," "down," etc. are merely used for convenience in describing the various embodiments of the present invention. The embodiments of the present invention may be oriented in various ways. For example, the diagrams, apparatuses, etc. shown in the drawing figures may be flipped over, rotated by 90° in any direction, reversed, etc.

For purposes of the present invention, a value or property is "based" on a particular value, property, the satisfaction of a condition or other factor, if that value is derived by performing a mathematical calculation or logical decision using that value, property, the satisfaction of a condition or other factor.

For purposes of the present invention, the term "antimicrobial" refers to a material that kills or inhibits the growth of microorganisms such as bacteria, viruses, fungi, molds or protozoans.

For purposes of the present invention, the term "antimicrobial organometallic additive" refers to an organometallic additive that imparts antimicrobial properties to a product of which the antimicrobial organometallic additive is a part or increases the antimicrobial properties of a product of which the antimicrobial organometallic additive is a part.

For purposes of the present invention, the term "degree of antimicrobial activity" refers to the percentage reduction in Colony Forming Units (CFU) observed when a polymer product is subjected to JIS Z 2801 test protocol described below in the Examples section. For example, if a 99.99831% reduction in Colony Forming Units (CFU) is observed for a polymer product, the product has a 99.99831% degree of antimicrobial activity.

For purposes of the present invention, the term "dispersed throughout" refers to one or more antimicrobial organometallic additives being distributed relatively evenly throughout a polymer host matrix.

For purposes of the present invention, the term "long-chain fatty acid" refers to a fatty acid having an aliphatic tail of 13 or more carbon atoms.

For purposes of the present invention, the term "long-chain fatty acid group" refers to the ester group derived from a long-chain fatty acid. An example of a long-chain fatty acid group is a stearate group.

For purposes of the present invention, the term "majority" refers to a majority by molar amount. For example, if there were a mixture of antimicrobial organometallic additives comprising 1.0 mole of cupric stearate and 1.0 mole of silver stearate present in a polymer product, 0.1 total moles of metals in a UV absorber dispersed throughout the polymer product and 0.2 moles of metal ions in a color in the polymer product, the antimicrobial organometallic additives would constitute a majority of the metallic species in the polymer product: 2.0 total moles of antimicrobial organometallic additives to 0.3 total moles of metallic species from other sources dispersed throughout the polymer.

For purposes of the present invention, the term "metallic species" refers to the metals, metal ions and metal-containing compounds present in a polymer product, depending on the polymer product. In addition to the metals in the antimicrobial organometallic additive of the present invention, polymer products of the present invention may also include metallic species that are metals, metal ions and metal-containing compounds such as metal salts, metal oxides, organometallic oxides, etc.

For purposes of the present invention, the term "organometallic additive" refers to a compound including a metal bound to an organic radical, where the metal species has a valence state of +1, +2, +3, etc.

For purposes of the present invention, the term "polymer host matrix" refers to a polymer or mixtures of polymers in which one or more antimicrobial organometallic additives are dispersed. A polymer may be a copolymer. A polymer host matrix includes components in addition to the polymer that do not react with the organometallic additives dispersed in the polymer host matrix. For example, the polymer host matrix may be fiberglass which comprises a polymer having dispersed therein glass fibers. Other fibers, such as carbon or graphene, metals and ceramics may also be used, as well as polymer fibers such as Kevlar® (DuPont's registered trademark for a para-aramid synthetic fiber).

For purposes of the present invention, the term "room temperature" refers to a temperature of from about 20° C. to about 25° C.

For purposes of the present invention, the term "a solid solution in a polymer host matrix" refers to an organometallic additive mechanically dispersed throughout and suspended within the polymer host matrix.

For purposes of the present invention, the term "sparingly soluble in water" refers to a substance having a solubility of 0.1 g per 100 ml of water to 1 g per 100 ml of water. Unless specified otherwise, the term "sparingly soluble" and "sparingly soluble in water" are used interchangeably in the description of the invention below to refer to substances that are sparingly soluble in water.

For purposes of the present invention, the term "thermosetting powder" refers to a powder that when applied and subjected to heat will melt, flow and chemically crosslink to form a film coating on a substrate. Thermosetting powders are primarily composed of relatively high molecular weight solid resins and a crosslinker. The primary resins used in the formulation of a thermosetting powder are: epoxy, polyester and acrylic. These primary resins may be used with different crosslinkers to produce a variety of powder coatings.

For purposes of the present invention, the term "thermoset powder coating" refers to a film coating formed by melting, flowing and chemically crosslinking a thermosetting powder. Chemical reactions during the curing cycle of a thermoset powder coating create a polymer network which may provide resistance to coating breakdown. Once cured and crosslinked, this polymer network will not melt and flow again if heat is applied.

For purposes of the present invention, the term "water insoluble" refers to a substance that has a solubility of less than 0.1 g per 100 ml of water.

Description

Because material surfaces may become contaminated with disease-causing agents, there is a need for materials with anti-bacterial, anti-virus, anti-fungal, anti-mold, etc. functionality; these are generally referred to as antimicrobials. Polymeric materials made from organic materials, inorganic materials or organic-inorganic material blends are ubiquitous in the environment, and if made to reduce antimicrobial disease-causing agents would play a valuable role in producing a healthier environment.

Three general classes of art for producing antimicrobial bulk polymers and polymer surfaces using additive systems currently exist: (1) nanoscale metal particles, (2) metal aluminosilicates, and (3) organic compounds. Although this art has demonstrated some utility it suffers from several limitations of which the following are the most often cited:
   (1) wears out due to repeated handling, washing or scrubbing of surface applied materials,
   (2) renders the bulk material not recyclable,
   (3) does not confer significant antimicrobial resistance,
   (4) narrow range of effectiveness against antimicrobial agents,
   (5) is toxic to viruses and molds with potential toxicity to humans at the levels employed,
   (6) modification required of existing plastic product manufacturing, equipment or processes,
   (7) post-production steps required for surface coating,
   (8) incomplete coverage/coating due to "hidden" surfaces,
   (9) is incompatible with critical geometries, such as products having micro-scale tolerances or dimensions.

In addition to the above-mentioned limitations of the existing art, the current products employing metal and aluminosilicate antimicrobial additives: (a) are costly, (b) have final product process-related issues such as reduced time-to-fabrication tooling wear out, therefore requiring more frequent tool replacement, and (c) require novel chemical moieties as surface ligands to help disperse and keep the particles from settling or agglomerating. Furthermore, current products employ organic antimicrobial additives that cannot be readily incorporated with many organic materials since these antimicrobial additives are: (a) chemically aggressive and inhibit the reaction processes of many thermosets and (b) degrade the mechanical, thermal and optical properties of many thermoplastics and thermosets.

An example of existing art appears in United States Patent Application No. 2011/0002872 to Ohashi et al., but this patent application does not describe the final form of the product that integrates the antimicrobial invention, but instead describes a conversion process (e.g., thermal decomposition) of a fatty acid metal salt for forming ultrafine metal particles that can be dispersed in a resin for further processing.

In one embodiment, the present invention provides a polymer product comprising a polymer host matrix having dispersed therein at least one antimicrobial organometallic additive or a blend of antimicrobial organometallic additives that impart antimicrobial properties to the bulk and surface of the polymer host matrix.

In one embodiment, the present invention provides uniformly dispersed antimicrobial functionality in a variety of host matrix polymer materials and a broad range of form factors. For example, the dispersed antimicrobial organometallic additives may be used to impart antimicrobial properties to the bulk and surface of a polymer host matrix in the form of bulk polymer products, film polymer products, sheet polymer products, polymer coating products, coated polymer products, composite polymer products, fibrous polymer products, a rod polymer products, core-containing polymer products and other types of polymer products.

In one embodiment, the present invention provides a polymer product comprising a polymer host matrix having dispersed therein at least one distributed metal type of antimicrobial organometallic additive or a blend of antimicrobial organometallic additives of more than one type of metal, said antimicrobial organometallic additives imparting antimicrobial properties to the bulk polymer products, film polymer products, sheet polymer products, polymer coating products, coated polymer products, composite polymer products, fibrous polymer products, a rod polymer products, core-containing polymer products and other types of polymer products.

In one embodiment of the present invention, the antimicrobial organometallic additive is about 0.008% to about 3% by volume of the total volume of the mixture of the antimicrobial organometallic additive in the polymer host matrix. In one embodiment of the present invention, the antimicrobial organometallic additive is about 0.008% to about 2.5% by volume of the total volume of the mixture of the antimicrobial organometallic additive in the polymer host matrix. In one embodiment of the present invention, the antimicrobial organometallic additive is about 0.008% to about 2% by volume of the total volume of the mixture of the antimicrobial organometallic additive in the polymer host matrix.

In one embodiment of the present invention, the blend of the antimicrobial organometallic additive is about 0.008% to about 3% by volume of the total volume of the mixture of the antimicrobial organometallic additive in the polymer host matrix. In one embodiment of the present invention, the blend of the antimicrobial organometallic additive is about 0.008% to about 2.5% by volume of the total volume of the mixture of the antimicrobial organometallic additive in the polymer host matrix. In one embodiment of the present invention, the blend of the antimicrobial organometallic additive is about 0.008% to about 2% by volume of the total volume of the mixture of the antimicrobial organometallic additive in the polymer host matrix.

In one embodiment, the present invention provides the ability to integrate one or more antimicrobial organometallic additives comprised of metals that are compatible with a variety of host matrix polymer materials that can be processed using conventional manufacturing equipment to fabricate various types of polymer products. In one embodiment of the present invention, the antimicrobial organometallic additives form a solid solution with the polymer host matrix and are distributed homogeneously throughout the polymer. Furthermore, the polymer host matrix may be an organic material, an inorganic material (e.g., silicone, etc.) or an organic-inorganic material blend. Also, the polymer host matrix may demonstrate the physical properties of a solid material, a liquid material, or a material having both solid-like and liquid-like physical properties.

In one embodiment of the present invention, an antimicrobial organometallic additive is an organic chemical moiety chemically bonded to a metal, either covalently or ionically. The chemical structure provides for enhanced miscibility throughout the polymer host matrix to produce various types of polymer products. Organic chemical moieties that may be bound to a metal in an antimicrobial organometallic additive of the present invention include but are not limited to the following chemical moieties: hydrocarbons, acetates, stearates, laureates, palmitates, oleates, abietates, fatty acids, etc.

Metals that may be used in the antimicrobial organometallic additives of the present invention include, but are not limited to, copper (Cu), silver (Ag), gold (Au), iridium (Ir), palladium (Pd), platinum (Pt), iron (Fe), nickel (Ni), cobalt (Co), zinc (Zn), niobium (Nb), ruthenium (Ru), rhodium (Rh), tellurium (Te), antimony (Sb), bismuth (Bi), tin (Sn), gallium (Ga), indium (In), titanium (Ti), vanadium (V), chromium, (Cr), manganese (Mn), molybdenum (Mo), tungsten (W), tantalum (Ta), hafnium (Hf), zirconium (Zr), scandium (Sc), and yttrium (Y), aluminum (Al), cadmium (Cd), mercury (Hg), thalium (Tl), lead (Pb), selenium (Se).

Metals that may be used in the antimicrobial organometallic additives of the present invention include alkali metals and alkali earth metals including, but are not limited to lithium (Li), sodium (Na), potassium (K), rubidium (Rb) cesium (Cs), beryllium (Be), magnesium (Mg), calcium (Ca), strontium (Sr), and barium (Ba).

Metals for the antimicrobial organometallic additives may be selected based on required functionality (e.g., anti-bacterial, anti-virus, anti-fungal, anti-mold, etc.) and may be chosen from the categories of transition metals, post-transition metals, metalloids, lanthanides, actinides, rare earth metals, alkaline earth metals, and alkali metals.

Suitable polymers that may be used in the polymer host matrix of the polymer products of the present invention include thermoplastics and thermosets and mixtures thereof.

In one embodiment of the present invention, the polymer host matrix may comprise a thermoplastic such as polyethylene (PE), polypropylene (PP), polycarbonate (PC), polystyrene (PS), polyamide (PA), polybutylene terephthalate (PBT), polyethylene terephthalate (PET), wax (e.g., paraffin, etc.), etc. In one embodiment, the polymer host matrix polymer may be a blend comprising more than one thermoplastic.

In one embodiment of the present invention, the polymer host matrix may comprise a thermoset plastic such as an epoxy, a phenolic, a cyanate ester, a bismaleimide, a polyimide, an acrylic, a silicone, a urethane, a latex, etc. In one embodiment, the polymer host matrix polymer may be a blend comprising more than one thermoset.

In one embodiment of the present invention, the polymer host matrix may comprise a polyurethane. The polymer host matrix may be a one-part polyurethane liquid polymer or a two-part polyurethane liquid polymer. The polyurethane polymer host matrix may be air cured, thermally cured, or UV-radiation cured.

In one embodiment of the present invention, the polymer host matrix may comprise a stable dispersion (emulsion) of polymer microparticles in an aqueous medium such as, but not limited to natural and synthetic latexes. The polymer host matrix may be a single polymer, a polymer blend, a co-polymer, or a co-polymer blend.

In one embodiment of the present invention, the polymer host matrix may comprise a mixture of a polymer and other materials such as glass. For example, the host matrix may be fiberglass which is a plastic matrix reinforced with fine glass fibers.

In various embodiments of the present invention, the polymer host matrix of the present invention may be formulated to achieve specific materials properties e.g., optical (clarity, refractive index, color, transparency), mechanical (elongation, glass transition temperature, coefficient of thermal expansion, elastic and shear modulus, toughness, adhesion, surface roughness), rheological (viscosity, melt flow index, surface energy, etc.), electrical (dielectric strength) and antimicrobial efficacy as required for optimal end product performance.

During thermal processing of the polymer host matrix and the antimicrobial organometallic additive, the antimicrobial organometallic additive may be converted to an organometallic-oxide.

In one embodiment, the present invention may be used as a bulk polymer product. In one embodiment, the present invention may be used as a polymer film. In one embodiment, the present invention may be used as a polymer sheet.

Bulk polymer products such as but not limited to master blends, toys, electronic housings, automotive interior panels, airplane passenger compartment structures, dental appliances such as mouth protectors, mouth guards, dentures and retainers, corrective vision devices (contact lenses, contact lens storage containers, eye glass frames), windows, aquarium walls, soap dispensers, paper towel dispensers, toilet paper dispensers, portable toilets, and portable washing stations. In these products, the host matrix bulk polymer provides substantial structural integrity for the device or application.

Film polymer products include but are not limited to flexible wrapping agents, film coats, and laminates. These products may have surface treatments to provide static or chemical adhesion as commonly used for promotional advertising, and marketing posters and labels. Film materials may be used in combination with touch screens and displays. Another example of a film polymer product is currency (banknotes). Furthermore, the film may be transparent, contain graphic art, text, or a combination of these. In these products, the film polymer provides little structural integrity to the device, but acts as a barrier or as a carrier of graphic information. In one embodiment, the film material is less than 0.1 mm thick.

Figure 2:
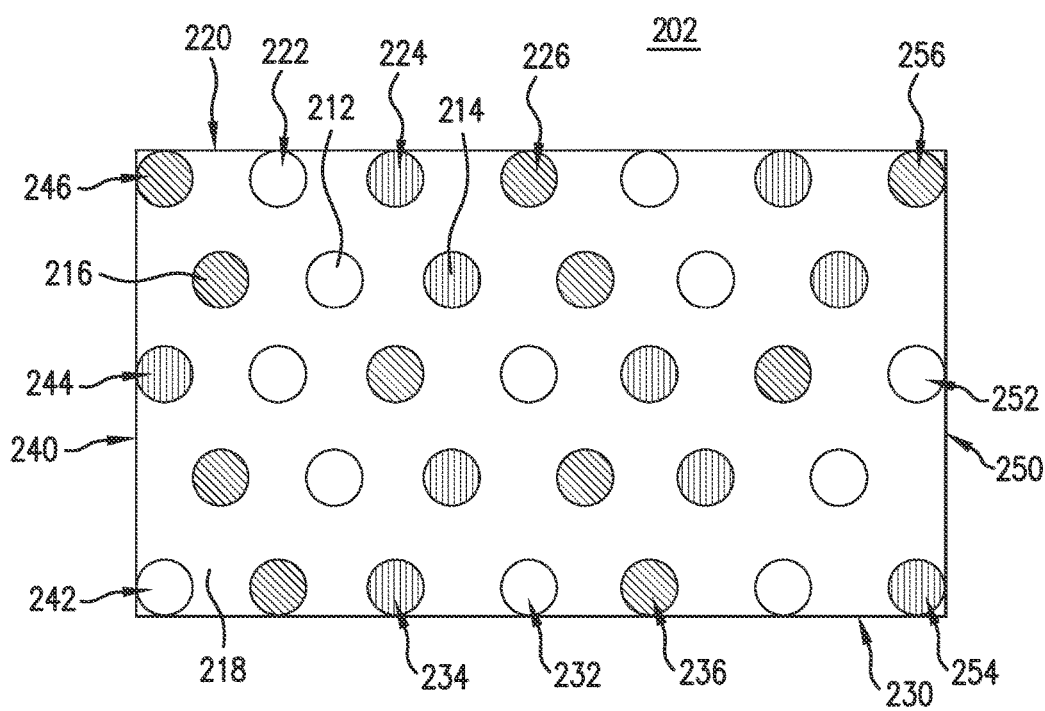
FIG. 2 is a schematic drawing of a polymer product having dispersed therein three organometallic additives according to one embodiment of the present invention.

FIGS. 1 and 2 illustrate in schematic form polymer products that each may be a bulk polymer product, a film polymer product or a sheet polymer product, depending on factors such as the dimensions of the polymer product, the polymer host matrix used, the physical properties of the polymer product, etc.

FIG. 1 depicts a polymer product 102 having dispersed therein an antimicrobial organometallic additive 112 distributed uniformly throughout a polymer host matrix 118. Some antimicrobial organometallic additive 112 resides at an upper surface 122 and a lower surface 124, as indicated by arrows 132 and 134, respectively. Some antimicrobial organometallic additive 112 resides at a left surface 142 and a right surface 144, as indicated by arrows 152 and 154, respectively.

FIG. 2 depicts a polymer product 202 having dispersed therein antimicrobial organometallic additives 212, 214, 216 distributed uniformly throughout a polymer host matrix 218. Antimicrobial organometallic additives 212, 214, 216 are different from each other. Some antimicrobial organometallic additives 212, 214 and 216 reside at an upper surface 220 as indicated by arrows 222, 224 and 226, respectively. Some antimicrobial organometallic additives 212, 214 and 216 reside at a lower surface 230 as indicated by arrows 232, 234 and 236, respectively. Some antimicrobial organometallic additives 212, 214 and 216 reside at a left surface 240 as indicated by arrows 242, 244 and 246, respectively. Some antimicrobial organometallic additives 212, 214 and 216 reside at a right surface 250 as indicated by arrows 252, 254 and 256, respectively.

Although one antimicrobial organometallic additive is shown in FIG. 1 and three different antimicrobial organometallic additives are shows in FIG. 2, a polymer product of the present invention may include any number of different antimicrobial organometallic additives. The metal part of each of the antimicrobial organometallic additives may be the same or different and/or the organic part of each of the antimicrobial organometallic additives may be the same or different.

The polymer product of FIG. 1 and/or FIG. 2 may have virtually any size or shape. For example, polymer products of FIG. 1 and/or FIG. 2 may be a block of material, a film, a sheet, etc.

A polymer product of the present invention that is a block of material may be made in various shapes such as spherical, rectangular box-shaped, cube-shaped, ellipsoid-shaped, cone-shaped, pyramidal, rod-shaped, ring-shaped, disks, rectangular plate-shaped, irregularly shaped, etc. A spherical or nearly spherical polymer product may be used in balls for purifying liquids such as but not limited to water and water-based fruit juices and forming master batches for draw-down during manufacture of the final polymer product. A spherical or nearly spherical polymer product may be fabricated with different densities so that polymer product may float at different levels in a liquid environment.

In one embodiment, the polymer product of FIG. 1 and/or FIG. 2 may be a bulk polymer product that is at least 0.01 mm thick.

In one embodiment, the polymer product of FIG. 1 and/or FIG. 2 may be a film polymer product having a thickness of less than or equal to 1.0 mm.

In one embodiment, the polymer product of FIG. 1 and/or FIG. 2 may be a bulk product or a sheet. For example, the polymer product may be a bulk or sheet product used separately or in combination with items such as but not limited to mass transit windows, building windows, and aquarium walls. These sheet products may have surface treatments to provide static or chemical adhesion to an underlying transparent material such as but not limited to glass, polycarbonate, acrylics and poly(methyl methacrylate). In these products, the sheet polymer provides limited structural integrity to the device and acts as a barrier. Examples of a film polymer product used separately are bags (e.g., food, waste management), privacy curtains (hospital rooms, examining rooms, etc.) and gloves (e.g., hygiene, contamination protection). Furthermore, the sheet may be transparent, contain graphic art, text, or a combination of both. In one embodiment of the present invention, the sheet polymer product is greater than 0.01 mm and less than or equal to 10 mm thick.

In one embodiment the present invention provides polymer coatings comprising one or more antimicrobial organometallic additives uniformly dispersed in a polymer material. Such coatings may have a variety of uses such as for powder coats, paints, shrink wraps, films, etc. In polymer coatings, the polymer coating may act as a surface protector and barrier. The polymer coatings of the present invention may be used on a variety of substrates such as carts, hospital gurneys, desks, chairs, metal gratings, shelving (e.g., refrigerator, produce, dairy, candy, and health care products), filters, and corrugated metal such as used for architectural wall finishing, etc. Polymer coatings of the present invention may also be coated on substrates such as gratings, animal cages, livestock fencing, animal feeding containers (bowls, troughs, plates, dispensers), filters, architectural wall finishing, privacy walls in bathrooms, hand dryers, hand rails and escalator guard rails). A polymer coating of the present invention may be transparent, translucent or opaque and may be colored with dyes (e.g., organic polymers, inorganic suspensions). A polymer coating host matrix that is transparent has a refractive index of at least 1.1 at 633 nm with optical transmission of >90% from 375 to 600 nm. In one embodiment of the present invention, a coating may be less than 1 mm thick.

A polymer coating of the present invention may be formed by mixing one or more antimicrobial organometallic additive in powder form with a polymer host matrix material in powder form, such as a thermosetting powder, to form a mixture in which the one or more antimicrobial organometallic additives are dispersed throughout the mixture. The mixture may then be heated to melt the mixture and form a polymer coating product in which the one or more antimicrobial organometallic additives are suspended in the polymer host. The coating product may be heated in place on the substrate to form a coating or the coating product may be heated and then applied to the substrate as a coating.

A polymer coating of the present invention may be formed by mixing one or more antimicrobial organometallic additive in powder form with a polymer host matrix material in liquid form to form a mixture in which the one or more antimicrobial organometallic additives are dispersed throughout the liquid. The liquid mixture may then be applied to a substrate to form a polymer coating product in which the one or more antimicrobial organometallic additives are suspended in the polymer host. The coating product may be heated in place on the substrate to form a coating, polymerized on the substrate using ultraviolet radiation (UV) to form a coating, dried via evaporation of solvent to form a coating, polymerized on the substrate via chemical reactions (i.e., curing) to form a coating. Examples of polymer host materials are latex paints, oil-based paints, 1-part polyurethane, 2-part polyurethane, 1-part epoxy, 2-part epoxy, etc.

Figure 3:
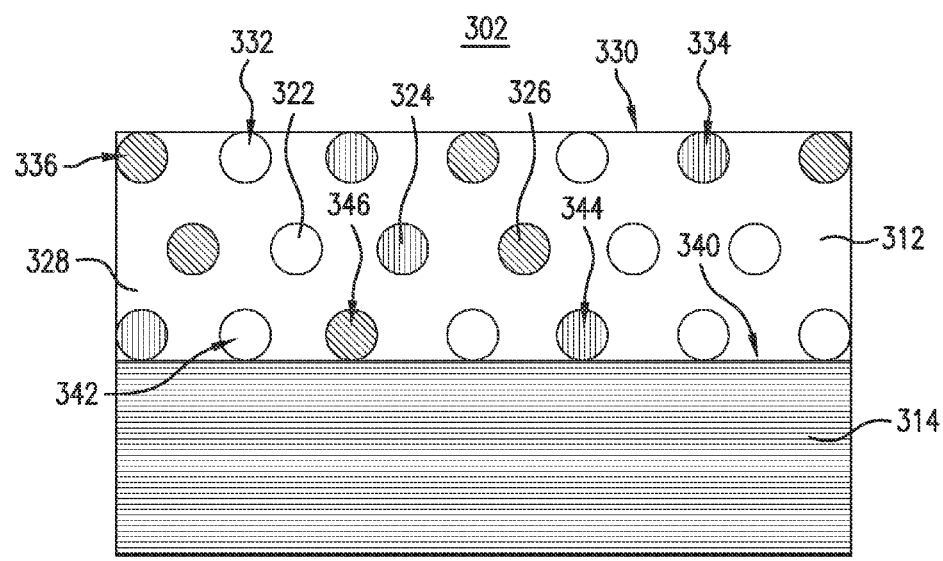
FIG. 3 is a schematic drawing of a polymer coating having dispersed therein three organometallic additives on a substrate according to one embodiment of the present invention.

FIG. 3 shows a polymer coated substrate 302 according to one embodiment of the present invention. Polymer coated substrate 302 comprises a polymer coating 312 coated on a substrate 314. Polymer coating 312 contains a blend of three different antimicrobial organometallic additives, i.e., antimicrobial organometallic additives 322, 324 and 326, dispersed uniformly throughout a polymer host matrix 328 of polymer coating 312. Antimicrobial organometallic additives 322, 324 and 326 are present at a surface 330 of polymer coating 312, as shown by arrows 332, 334 and 336, respectively, and at an interface 340 between polymer coating 312 and substrate 314, as shown by arrows 342, 344 and 346, respectively. Polymer coating 312 is chemically and/or mechanically bonded to the substrate 314 at interface 340.

Although three antimicrobial organometallic additives are shown in the polymer coating of FIG. 3, there may be one, two, three, four or more antimicrobial organometallic additives in a polymer coating of the present invention. The antimicrobial organometallic additives may be of the same chemistry or they may be of different chemistries.

The substrate on which a polymer coating of the present invention is coated may be a metal such as aluminum, titanium, copper, brass, bronze, nickel, pewter, silver, gold, stainless steel, carbon steel, steel, molybdenum, Inconel, alloys of these metals, etc., a ceramic such as aluminum oxide (sapphire), ceramic tile, glass (borosilicate, soda-lime-silicate, quartz), granite, marble, etc., a plastic such as a vinyl polymer, polycarbonate, polyethylene, polypropylene, PEN, PET, wax (paraffin) etc., or any other type of suitable substrate material.

In one embodiment, the present invention provides a composite product including one or more antimicrobial organometallic additives in a polymer host matrix. Such composite products include fabrics, bandages, tents, mats (e.g., wrestling, gymnastics, bathroom), tarps, clothing used by first responders, clothing used by campers, clothing used for recreational purposes, work clothing, sports clothing, uniforms, space suits, military operations personnel, healthcare professionals, and hospital staff (e.g., surgical garments), etc. In a composite product of the present invention, a discrete layer or film comprising the one or more antimicrobial organometallic additives in a polymer host matrix is integrated into the composite product. A polymer layer comprising one or more antimicrobial organometallic additives in a polymer host matrix acts as a surface protector and barrier. The barrier functionality of such a polymer layer may include transmission of liquid such as water, and gases such as water vapor and air. In one embodiment, such a polymer layer is less than 1 mm thick.

Figure 4:
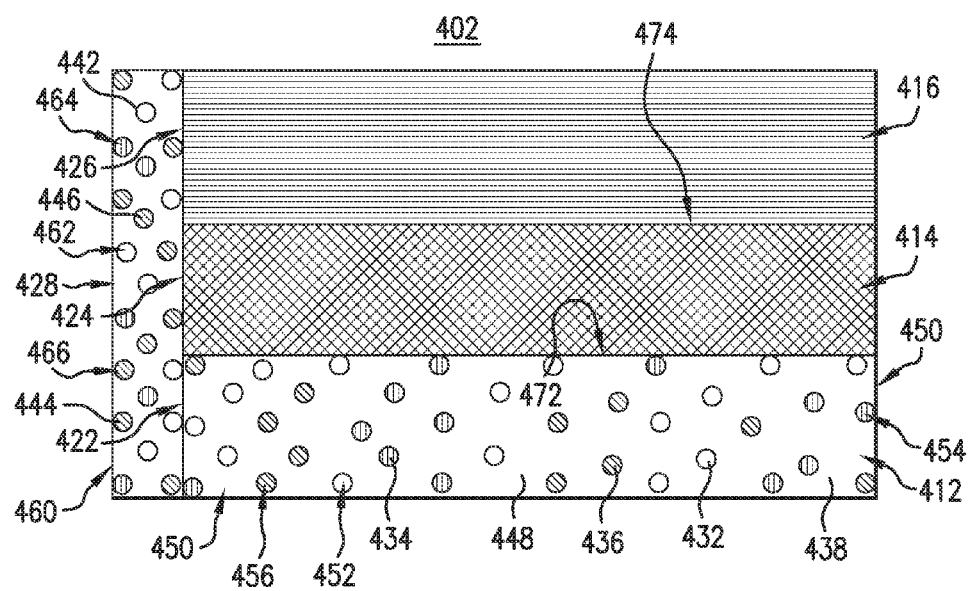
FIG. 4 is a schematic drawing of a composite product including a polymer layer having dispersed therein three organometallic additives and a polymer edge coating having dispersed therein three organometallic additives according to one embodiment of the present invention.

FIG. 4 shows a composite product 402 according to one embodiment of the present invention. Composite product 402 includes a polymer layer 412, an inner layer 414 and an outer layer 416. Coated on edges 422, 424 and 426, respectively, of polymer layer 412, inner layer 414 and outer layer 416 is an edge coating 428. Polymer layer 412 comprises a blend of three different antimicrobial organometallic additives, i.e., antimicrobial organometallic additives 432, 434 and 436, dispersed uniformly throughout a polymer host matrix 438. Edge coating 428 comprises a blend of three different antimicrobial organometallic additives, i.e., antimicrobial organometallic additives 442, 444 and 446, dispersed uniformly throughout a polymer host matrix 448. Antimicrobial organometallic additives 432, 434 and 436 are also present at exterior surfaces 450 of polymer host matrix 438 as shown by arrows 452, 454 and 456, respectively. Antimicrobial organometallic additives 442, 444 and 446 are present at exterior surface 460 of polymer host matrix 448 as shown by arrows 462, 464 and 466. An interface 472 provides mechanical and/or chemical bonding between polymer layer 412 and inner layer 414. An interface 474 provides mechanical and/or chemical bonding between inner layer 414 and outer layer 416.

Although the edge coating in FIG. 4 is shown as covering the edges of the polymer layer, the inner layer and the outer layer, in some embodiments of the present invention, the edges of only one or two of these layers may be coated with the edge coating.

Although in FIG. 4, an edge coating is only shown on the left-hand side of the composite product, in some embodiments of the present invention, there may be an edge-coating on both the left-hand and right-hand side of the composite product. The edge coatings on each side may be the same or different.

Although three antimicrobial organometallic additives are shown in the polymer layer and the edge coating of FIG. 4, there may be one, two, three, four or more antimicrobial organometallic additives in an edge coating or polymer layer of a composite product of the present invention. The antimicrobial organometallic additive may be the same chemistry or different chemistry.

The polymer host matrix and the antimicrobial organometallic additives of the polymer layer and the edge coating may be the same or different.

In one embodiment of the present invention, the polymer layer of a composite product may have a thickness of 10 mm or less.

In one embodiment of the present invention the outer layer and inner layer of the composite product may be porous to allow transmission of liquids such as water, and gases such as water vapor and air to the polymer layer.

The inner and outer layers may be made from a variety of materials including woven or non-woven textiles such as silk, cotton, polymer textiles or blends thereof, high strength plastics such as but not limited to poly-paraphenylene terephthalamide (e.g., Kevlar®), and metals such as but not limited to aluminum, titanium, copper, brass, bronze, nickel, pewter, silver, gold, stainless steel, carbon steel, steel, molybdenum, Inconel, alloys of these metals, etc., a ceramic such as aluminum oxide (sapphire), ceramic tile, glass (borosilicate, soda-lime-silicate, quartz), granite, marble, etc., a plastic such as a vinyl polymer, polycarbonate, polyethylene, polypropylene, PEN, PET, wax (paraffin) etc., or any other type of suitable substrate material.

Figure 5:
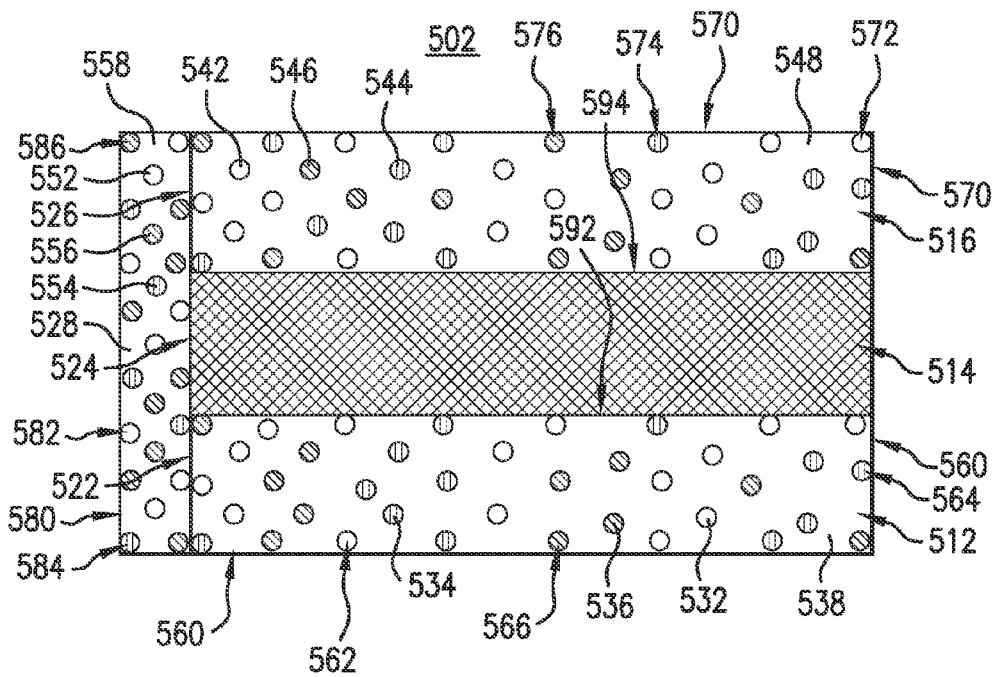
FIG. 5 is a schematic drawing of a composite product including two polymer layers having dispersed therein three organometallic additives and a polymer edge coating having dispersed therein three organometallic additives according to one embodiment of the present invention.

FIG. 5 shows a composite product 502 according to one embodiment of the present invention. Composite product 502 includes a lower polymer layer 512, an inner layer 514 and an upper polymer layer 516. Coated on edges 522, 524 and 526, respectively, of lower polymer layer 512, inner layer 514 and upper polymer layer 516 is an edge coating 528. Lower polymer layer 512 comprises a blend of three different antimicrobial organometallic additives, i.e., antimicrobial organometallic additives 532, 534 and 536, dispersed uniformly throughout a polymer host matrix 538. Upper polymer layer 516 comprises a blend of three different antimicrobial organometallic additives, i.e., antimicrobial organometallic additives 542, 544 and 546, dispersed uniformly throughout a polymer host matrix 548. Edge coating 528 comprises a blend of three different antimicrobial organometallic additives, i.e., antimicrobial organometallic additives 552, 554 and 556, dispersed uniformly throughout a polymer host matrix 558. Antimicrobial organometallic additives 532, 534 and 536 are present at exterior surfaces 560 of polymer host matrix 538 as shown by arrows 562, 564 and 566, respectively. Antimicrobial organometallic additives 542, 544 and 546 are present at exterior surfaces 570 of polymer host matrix 548 as shown by arrows 572, 574 and 576, respectively. Antimicrobial organometallic additives 552, 554 and 556 are present at exterior surface 580 of polymer host matrix 548 as shown by arrows 582, 584 and 586. An interface 592 provides mechanical and/or chemical bonding between lower polymer layer 512 and inner layer 514. An interface 594 provides mechanical and/or chemical bonding between inner layer 514 and upper polymer layer 516.

Although the edge coating in FIG. 5 is shown as covering the edges of the lower polymer layer, the inner layer and the upper polymer layer, in some embodiments of the present invention, the edges of only one or two of these layers may be coated with the edge coating.

Although in FIG. 5, an edge coating is only shown on the left-hand side of the composite product, in some embodiments of the present invention, there may be an edge-coating on both the left-hand and right-hand side of the composite product. The edge coatings on each side may be the same or different.

Although three antimicrobial organometallic additives are shown in the lower polymer layer, upper polymer layer and the edge coating of FIG. 5, there may be one, two, three, four or more antimicrobial organometallic additives in an edge coating or polymer layer of a composite product of the present invention. The antimicrobial organometallic additive may be the same chemistry or different chemistry.

The polymer host matrix and the antimicrobial organometallic additives of the lower polymer layer, upper polymer layer and the edge coating may be the same or different for each of the lower polymer layer upper polymer layer and the edge coating.

In one embodiment of the present invention, the lower polymer layer and/or upper polymer layer of a composite product may have a thickness of 1 mm or less.

In one embodiment of the present invention the inner layer of the composite product may be porous to allow transmission of liquids such as water, and gases such as water vapor and air to the polymer layer.

The inner layer may be made from a variety of materials including woven or non-woven textiles such as silk, cotton or blends thereof, high strength plastics such as but not limited to poly-paraphenylene terephthalamide (e.g., Kevlar®), and metals such as but not limited to aluminum, titanium, copper, brass, bronze, nickel, pewter, silver, gold, stainless steel, carbon steel, steel, molybdenum, Inconel, alloys of these metals, etc., a ceramic such as aluminum oxide (sapphire), ceramic tile, glass (borosilicate, soda-lime-silicate, quartz), granite, marble, etc., a plastic such as a vinyl polymer, polycarbonate, polyethylene, polypropylene, PEN, PET, wax (paraffin) etc., or any other type of suitable substrate material.

Figure 6:
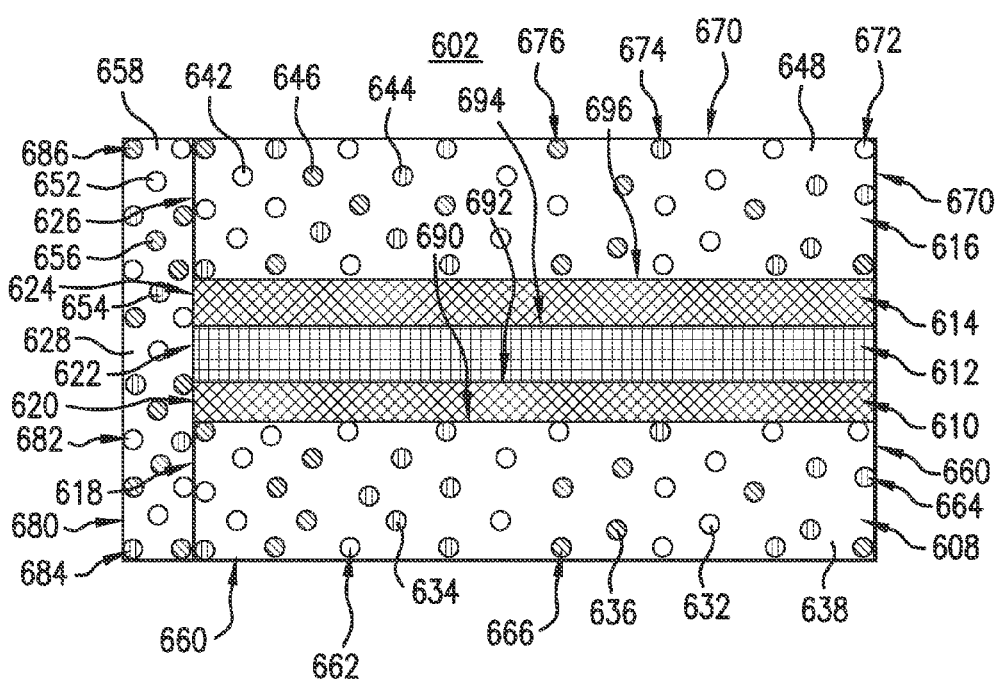
FIG. 6 is a schematic drawing of a composite product including two polymer layers having dispersed therein three organometallic additives and a polymer edge coating having dispersed therein three organometallic additives according to one embodiment of the present invention.

FIG. 6 shows a composite product 602 according to one embodiment of the present invention. Composite product 602 includes a lower polymer layer 608, a lower inner layer 610, a middle inner layer 612, an upper inner layer 614 and an upper polymer layer 616. Coated on edges 618, 620, 622, 624 and 626, respectively, of lower polymer layer 608, lower inner layer 610, middle inner layer 612, upper inner layer 614 and upper polymer layer 616 is an edge coating 628. Lower polymer layer 608 comprises a blend of three different antimicrobial organometallic additives, i.e., antimicrobial organometallic additives 632, 634 and 636, dispersed uniformly throughout a polymer host matrix 638. Upper polymer layer 616 comprises a blend of three different antimicrobial organometallic additives, i.e., antimicrobial organometallic additives 642, 644 and 646, dispersed uniformly throughout a polymer host matrix 648. Edge coating 628 comprises a blend of three different antimicrobial organometallic additives, i.e., antimicrobial organometallic additives 652, 654 and 656, dispersed uniformly throughout a polymer host matrix 658. Antimicrobial organometallic additives 632, 634 and 636 are present at exterior surfaces 660 of polymer host matrix 638 as shown by arrows 662, 664 and 666, respectively. Antimicrobial organometallic additives 642, 644 and 646 are present at exterior surfaces 670 of polymer host matrix 648 as shown by arrows 672, 674 and 676, respectively. Antimicrobial organometallic additives 652, 654 and 656 are present at exterior surface 680 of polymer host matrix 648 as shown by arrows 682, 684 and 686. An interface 690 provides mechanical and/or chemical bonding between lower polymer layer 608 and lower inner layer 610. An interface 692 provides mechanical and/or chemical bonding between lower inner layer 610 and middle inner layer 612. An interface 694 provides mechanical and/or chemical bonding between middle inner layer 612 and upper inner layer 614. An interface 696 provides mechanical and/or chemical bonding between upper inner layer 614 and upper polymer layer 616.

Although the edge coating in FIG. 6 is shown as covering the edges of the lower polymer layer, the lower inner layer, the middle inner layer, the upper inner layer and the upper polymer layer, in some embodiments of the present invention, the edges of only one, two, three or four of these layers may be coated with the edge coating.

Although in FIG. 6, an edge coating is only shown on the left-hand side of the composite product, in some embodiments of the present invention, there may be an edge-coating on both the left-hand and right-hand side of the composite product. The edge coatings on each side may be the same or different.

Although three antimicrobial organometallic additives are shown in the lower polymer layer, upper polymer and the edge coating of FIG. 6, there may be one, two, three, four or more antimicrobial organometallic additives in an edge coating or polymer layer of a composite product of the present invention. The antimicrobial organometallic additive may be the same chemistry or different chemistry.

The polymer host matrix and the antimicrobial organometallic additives of the lower polymer layer upper polymer layer and the edge coating may be the same or different for each of the lower polymer layer upper polymer layer and the edge coating.

In one embodiment of the present invention, the lower polymer layer and/or upper polymer layer of a composite product may have a thickness of 1 mm or less.

In one embodiment of the present invention, the lower inner layer, middle inner layer and/or upper middle layer of the composite product may be porous to allow transmission of liquids such as water, and gases such as water vapor and air to the polymer layer.

The lower inner layer, middle inner layer and/or upper middle layer may each be made from a variety of materials including woven or non-woven textiles such as silk, cotton, polymer textiles or blends thereof, high strength plastics such as but not limited to poly-paraphenylene terephthalamide (e.g., Kevlar®), and metals such as but not limited to aluminum, titanium, copper, brass, bronze, nickel, pewter, silver, gold, stainless steel, carbon steel, steel, molybdenum, Inconel, alloys of these metals, etc., a ceramic such as aluminum oxide (sapphire), ceramic tile, glass (borosilicate, soda-lime-silicate, quartz), granite, marble, etc., a plastic such as a vinyl polymer, polycarbonate, polyethylene, polypropylene, PEN, PET, wax (paraffin) etc., or any other type of suitable substrate material.

In one embodiment, the present invention may be a fiber polymer product. Fiber polymer products of the present invention may be used in various types of products such as floor coverings (e.g., carpets, rugs), artificial turf (e.g., residential, athletic, landscaping), window shades and draperies, privacy curtains, wall coverings (e.g., wall paper), seating upholstery, air filters, water filters, thread, fabric, cloth, clothing, textiles, etc.

In one embodiment of the present invention, a fiber polymer product may have a diameter of 10 mm or less.

In one embodiment, the present invention may be a rod polymer product. Rod polymer products of the present invention may be used in such products as a guard rails, hand rails (e.g., for a banister, escalator), door handles, grab bars, shower rods, shopping cart handles, extruded products, facemasks for helmets, electrical wiring, etc. The rod form may be modified to form belts, or have multiple surfaces, detents, notches, flats, indents, etc.

In one embodiment of the present invention, a rod polymer product may have a diameter of 10 mm or greater.

Figure 7:
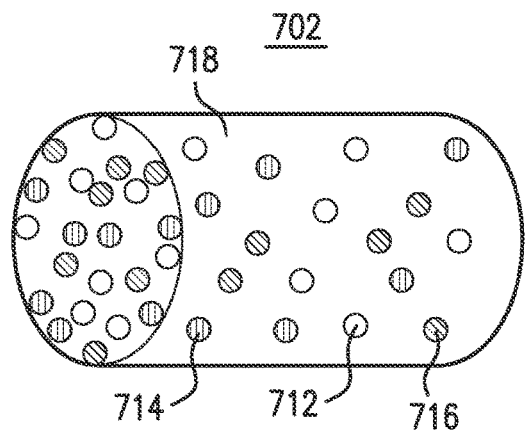
FIG. 7 is a schematic drawing of a elongated polymer product having dispersed therein three organometallic additives according to one embodiment of the present invention.
Figure 8:
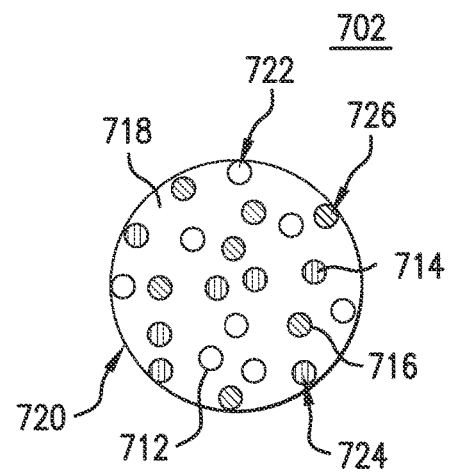
FIG. 8 is a cross-sectional view of the product of FIG. 7.

FIGS. 7 and 8 illustrate in schematic form an elongated polymer product having dispersed therein three antimicrobial organometallic additives according to one embodiment of the present invention. The elongated polymer product of FIGS. 7 and 8 may be a fiber polymer product or a rod-shaped polymer product, depending on factors such as the dimensions of the polymer product, the polymer host matrix used, the physical properties of the polymer product, etc.

FIGS. 7 and 8 depict an elongated polymer product 702 having dispersed therein antimicrobial organometallic additives 712, 714 and 716 distributed uniformly throughout a polymer host matrix 718. Antimicrobial organometallic additives 712, 714 and 716 are different from each other. Some antimicrobial organometallic additives 712, 714 and 716 reside at an outer surface 720 as indicated by arrows 722, 724 and 726, respectively.

Although three antimicrobial organometallic additives are shown in the polymer product of FIGS. 7 and 8, there may be one, two, three, four or more antimicrobial organometallic additives in a fiber polymer product or a rod polymer product of the present invention. The organometallic additive may be of the same chemistry or different chemistry Although the cross-sectional shape of the polymer product shown in FIGS. 7 and 8 is circular, a fiber polymer product or rod-shaped polymer product of the present invention may have any cross-sectional shape such as oval, triangular, square, rectangular, hexagonal, polygonal, I-shaped, U-shaped, star-shaped, asterix-shaped, multi-polygonal, multi-dimensional. etc.

In one embodiment, the present invention may be a reinforced fiber polymer product. Reinforced fiber polymer products of the present invention may be used in various types of products such as floor coverings (e.g., carpets, rugs), artificial turf (e.g., residential, athletic, landscaping), window shades and draperies, privacy curtains, wall coverings (e.g., wall paper), seating upholstery, air filters, water filters, electrical wiring, thread, fabric, cloth, clothing, textiles, etc.

In one embodiment of the present invention, a reinforced fiber polymer product may have a diameter of 10 mm or less.

In one embodiment, the present invention may be a rod polymer product. Rod polymer products of the present invention may be used in such product as a guard rails, hand rails (e.g., for a banister, escalator), door handles, grab bars, shower rods, shopping cart handles, extruded products, facemasks for helmets, electrical wiring, etc. The rod form may be modified to form belts, or have multiple surfaces, detents, notches, flats, indents, etc.

In one embodiment, a reinforced rod polymer product may have a diameter of 10 mm or greater.

Figure 9:
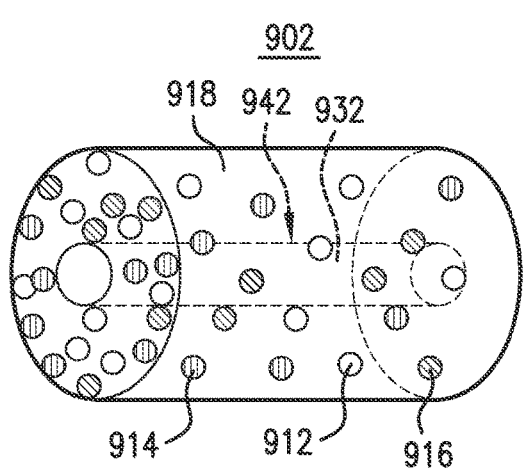
FIG. 9 is a schematic drawing of a reinforced polymer product having dispersed therein three organometallic additives according to one embodiment of the present invention.
Figure 10:
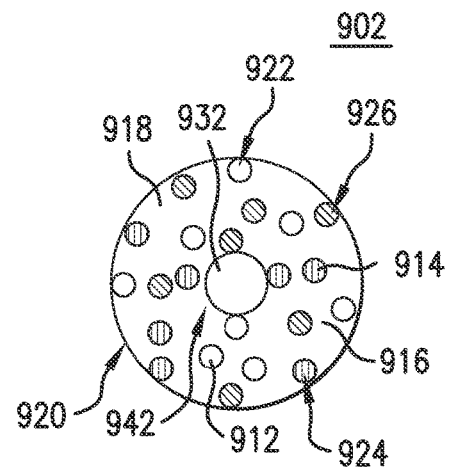
FIG. 10 is a cross-sectional view of the product of FIG. 9.

FIGS. 9 and 10 illustrate in schematic form a reinforced polymer product having dispersed therein three antimicrobial organometallic additives according to one embodiment of the present invention. The reinforced polymer product of FIGS. 9 and 10 may be a reinforced fiber polymer product or a reinforced rod-shaped polymer product depending on factors such as the dimensions of the polymer product, the polymer host matrix used, the physical properties of the polymer product, etc.

FIGS. 9 and 10 depict a reinforced polymer product 902 having dispersed therein antimicrobial organometallic additives 912, 914 and 916 distributed uniformly throughout a polymer host matrix 918. Antimicrobial organometallic additives 912, 914 and 916 are different from each other. Some antimicrobial organometallic additives 912, 914 and 916 reside at an outer surface 920 as indicated by arrows 922, 924 and 926, respectively. A support structure 932 runs through polymer product 902. An interface 942 provides mechanical and chemical bonding between the polymer host fiber matrix 918 and support structure 932.

Although three antimicrobial organometallic additives are shown in the reinforced polymer product of FIGS. 9 and 10, there may be one, two, three, four or more antimicrobial organometallic additives in a reinforced polymer product of the present invention. The antimicrobial organometallic additives may be the same chemistry or different chemistry.

Although the cross-sectional shape of the reinforced polymer product and support structure shown in FIGS. 9 and 10 is circular, a reinforced polymer product and/or support structure of the present invention may have any cross-sectional shape such as oval, triangular, square, rectangular, hexagonal, polygonal, I-shaped, U-shaped, star-shaped, asterix-shaped, multi-polygonal, multi-dimensional, etc. The reinforced polymer product and support structure may have the same or different cross-sectional shapes. The support structure may also be non-existent so that the resulting structure forms a hollow tube, pipe, or other structure with an opening substantially throughout its body.

The length of a support structure relative to a reinforced polymer product may be the same as the reinforced polymer product, shorter than the reinforced polymer product or longer than the reinforced polymer product. A reinforced polymer product may also include more than one support structure that may be arranged along the same axis in the reinforced polymer product and/or along different axes in the reinforced polymer product and/or scattered throughout the reinforced polymer product.

The support structure of a reinforced polymer product may form the bulk of a reinforced polymer product. The support structure of a reinforced polymer product may be made of various materials such as a metal, ceramic, a plastic material, etc. or combinations thereof, depending on the desired property of the reinforced polymer product.

Figure 11:
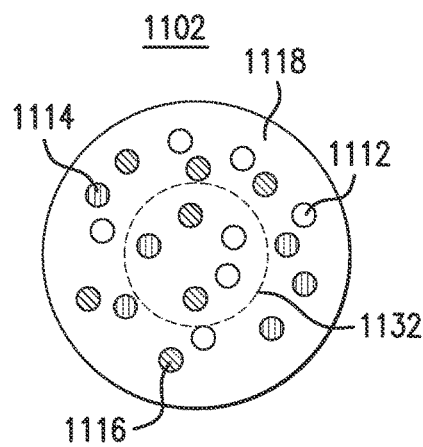
FIG. 11 is a schematic drawing of a spherical core-containing polymer product having dispersed therein three organometallic additives according to one embodiment of the present invention.
Figure 12:
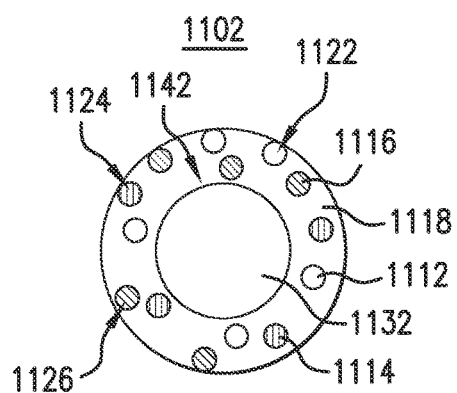
FIG. 12 is a cross-sectional view of the product of FIG. 11.
Figure 13:
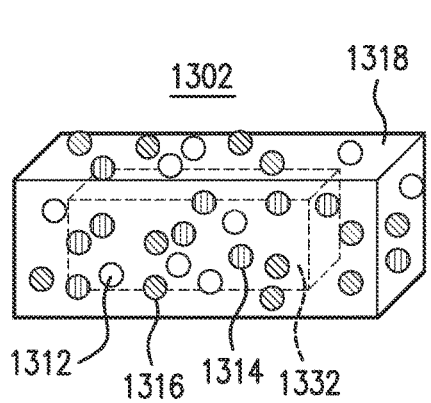
FIG. 13 is a schematic drawing of a rectangular box-shaped core-containing polymer product having dispersed therein three organometallic additives according to one embodiment of the present invention.
Figure 14:
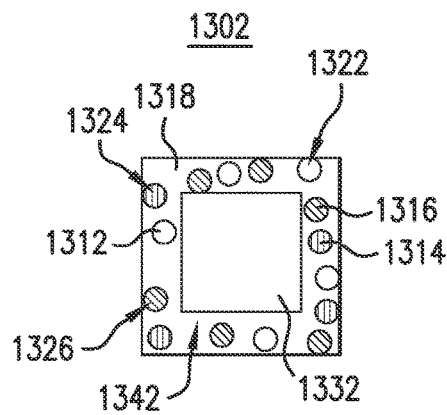
FIG. 14 is a cross-sectional view of the product of FIG. 13.

FIGS. 11, 12, 13 and 14 illustrate in schematic form two examples of core-containing polymer products of the present invention. FIGS. 11 and 12 illustrate a spherical-shaped core-containing polymer product having dispersed therein three antimicrobial organometallic additives according to one embodiment of the present invention. FIGS. 13 and 14 illustrate a rectangular box-shaped core-containing polymer product having dispersed therein three antimicrobial organometallic additives according to one embodiment of the present invention.

Spherical or nearly spherical products may be used in purifying liquids such as water, water-based fruit juices, etc. Pelletized polymer products used as the feedstock in the manufacture of final polymer products by thermal injection molding, extrusion, etc., can also have spherical or near spherical form. The spherical or nearly spherical products may be fabricated with different densities so that they may float at different levels in a liquid environment. Non-spherical shapes, such as but not limited to rods, rings, disks, rectangular plates, pyramidal and other geometries may also be used.

A polymer product of the present invention that is a core-containing polymer product may be made in various shapes such as spherical, rectangular box-shaped, cube-shaped, ellipsoid-shaped, cone-shaped, pyramidal, rod-shaped, ring-shaped, disks, rectangular plate-shaped, irregularly shaped, etc. A spherical or nearly spherical polymer product may be used in balls for purifying liquids such as but not limited to water, water-based liquids, water-based fruit juices, milk, etc. Pelletized polymer products used as the feedstock in the manufacture of final polymer products, for example, thermal injection molding, extrusion, etc., can also have spherical or near spherical form. A spherical or nearly spherical polymer product may be fabricated with different densities so that the polymer product may float at different levels in a liquid environment.

FIGS. 11 and 12 depict a spherical core-containing polymer product 1102 having dispersed therein antimicrobial organometallic additives 1112, 1114 and 1116 distributed uniformly throughout a polymer host matrix 1118. Antimicrobial organometallic additives 1112, 1114 and 1116 are different from each other. Some antimicrobial organometallic additives 1112, 1114 and 1116 reside at an outer surface 1120 as indicated by arrows 1122, 1124 and 1126, respectively. A core 1132 is located inside polymer product 1102 and may also contain antimicrobial organometallic additives or not. An interface 1142 provides mechanical and chemical bonding between the polymer host matrix 1118 and core 1132.

FIGS. 13 and 14 depict a rectangular box-shaped core-containing polymer product 1302 having dispersed therein antimicrobial organometallic additives 1312, 1314 and 1316 distributed uniformly throughout a polymer host matrix 1318. Antimicrobial organometallic additives 1312, 1314 and 1316 are different from each other. Some antimicrobial organometallic additives 1312, 1314 and 1316 reside at an outer surface 1320 as indicated by arrows 1322, 1324 and 1326, respectively. A core 1332 is located inside polymer product 1302 and may also contain antimicrobial organometallic additives or not. An interface 1342 provides mechanical and chemical bonding between the polymer host matrix 1318 and core 1332.

A core-containing polymer product of the present invention may have various shapes such as spherical (as shown in FIGS. 11 and 12), rectangular box-shaped (as shown in FIGS. 13 and 14), cube-shaped, ellipsoid-shaped, cone-shaped, pyramidal, rod-shaped, ring-shaped, disks, rectangular plate-shaped, irregularly shaped, multi-polygonal, multi-dimensional, etc. A spherical or nearly spherical core-containing polymer product may be Although three antimicrobial organometallic additives are shown in the core-containing polymer products of FIGS. 11, 12, 13 and 14 and there may be one, two, three, four or more antimicrobial organometallic additives in a reinforced polymer product of the present invention. The antimicrobial organometallic additive may be the same chemistry or different chemistry.

A core-containing polymer product of the present invention may have various shapes such as spherical (as shown in FIGS. 11 and 12), rectangular box-shaped (as shown in FIGS. 13 and 14), cube-shaped, ellipsoid-shaped, cone-shaped, pyramidal, rod-shaped, ring-shaped, disks, rectangular plate-shaped, irregularly shaped, multi-polygonal, multi-dimensional, etc. A spherical or nearly spherical core-containing polymer product may be used in balls for purifying liquids such as but not limited to water, water-based liquids, water-based fruit juices, milk, etc. Pelletized polymer products used as the feedstock in the manufacture of final polymer products, for example, thermal injection molding, extrusion, etc., can also have spherical or near spherical form. A spherical or nearly spherical polymer may be fabricated with different densities so that they may float at different levels in a liquid environment.

The antimicrobial organometallic additive in any of the polymer products and/or any portion and/or layer of a polymer product of the present invention may be at various ratios with respect to each other. For example, when a blend of three antimicrobial organometallic additives are dispersed in a polymer host matrix of the present invention, the ratio of the antimicrobial organometallic additives may be 1:1:1, 1:2:1, 2:3:4, or any other suitable ratio.

In one embodiment, the antimicrobial organometallic additives are a majority of the metallic species present in a polymer host matrix of a polymer product of the present invention. In some embodiments of the present invention there may be low levels of metals or metal ions present from other additives dispersed throughout the polymer host matrix (e.g., UV protectors, colorants, etc.). In some embodiments of the present invention, the antimicrobial organometallic additives may be the only metallic species present in a polymer host matrix of a polymer product of the present invention.

In one embodiment, the antimicrobial polymer products of the present invention include antimicrobial organometallic additives that are water insoluble or sparingly soluble in water. A single water insoluble or sparingly insoluble antimicrobial organometallic additive may be employed or mixtures of water insoluble and/or sparingly soluble antimicrobial organometallic additives may be employed. In one embodiment of the present invention, the water insoluble antimicrobial organometallic additives may comprise a long-chain fatty acid group as their organic component. Such compounds include, metal stearates and mixtures thereof. Suitable metal stearates that provide antimicrobial activity to a polymer product include, silver stearate, cupric stearate, zinc stearate, etc., and mixtures thereof. One advantage of using water insoluble antimicrobial organometallic additives having a long-chain fatty acid group as their organic component is that that they should provide long-lasting antimicrobial activity to polymer products, even when the polymer products are exposed to moisture or immersed in water. The water insolubility of such additives and the presence of the long-chain fatty acid group should cause such additives to stay bound and/or complexed in the polymer of the polymer product and not leach into the moisture or water. This is different than that for water soluble antimicrobial organometallic additives, for example, acetate based systems.

In one embodiment, the present invention provides a polyurethane product having antimicrobial activity that may be made by mixing one or more antimicrobial organometallic additives of the present invention with a liquid polyurethane at room temperature.

In one embodiment, the present invention provides a powder coat product, such as a thermoset powder coating. A thermoset powder coating may be formed by mixing one or more antimicrobial organometallic additives in powder form with a thermosetting powder to form a powder mixture. The powder mixture is then applied to a substrate and heated to melt, flow and chemically crosslink the components of the thermosetting powder in the powder mixture to form a thermoset film coating on the substrate. The thermoset coating has the one or more antimicrobial organometallic additives dispersed therein. The temperature that is used to form the thermoset film coating depends on the particular components of the thermosetting powder. In one embodiment, the temperature used to form the thermoset film coating is from 170° C. to 215° C.

In one embodiment of the present invention, the polymer host matrix may be paraffin wax. A paraffin wax product of the present may be formed by mixing one or more antimicrobial organometallic additives with liquid paraffin wax at temperature of 37° C. to 100° C. to form a paraffin wax product having the one or more antimicrobial organometallic additives dispersed throughout the polymer host matrix.

The present invention will now be described by way of example.

EXAMPLES

The testing of antimicrobial activity for the polymer samples in Examples 1, 2, 3, 4, 5, 6, 7, 8 and 9 below is performed using the Antimicrobial Test Laboratories' JIS Z 2801 Test for Antimicrobial Activity of Plastics. A summary of the JIS Z 2801 Test procedure is provided below:

(1) The test microorganism is prepared, usually by growth in a liquid culture medium.
(2) The suspension of test microorganism is standardized by dilution in a nutritive broth (this affords microorganisms the potential to grow during the test).
(3) Control and test surfaces are inoculated with microorganisms, in triplicate, and then the microbial inoculum is covered with a thin, sterile film. Covering the inoculum spreads it, prevents it from evaporating, and ensures close contact with the antimicrobial surface.
(4) Microbial concentrations are determined at "time zero" by elution followed by dilution and plating.
(5) A control is run to verify that the neutralization/elution method effectively neutralizes the antimicrobial agent in the antimicrobial surface being tested.
(6) Inoculated, covered control and antimicrobial test surfaces are allowed to incubate undisturbed in a humid environment for 24 hours.
(7) After incubation, microbial concentrations are determined Reduction of microorganisms relative to initial concentrations and the control surface is calculated.

Example 1

Composition 1. Silver stearate powder is added to a clear coat powder coat material supplied by The Finishing Company, Addison, Ill. Thermosetting powders are composed of relatively high molecular weight resins, typically blends of epoxy, polyester and acrylic, with crosslinking agents and color additives as required. Suppliers include DuPont, BASF, etc. The silver stearate powder and clear coat powder are then mixed vigorously to disperse the silver stearate powder in the clear coat powder and to form a powder blend. The powder blend is 2.5% silver stearate and 97.5% clear coat powder by volume. An approximately 5 ml sample of this powder blend is placed in an aluminum foil dish. The sample is heated at 380° F. for 10 minutes and then removed from the oven to cool. The sample is tested for antimicrobial activity using the JIS Z 2801 test procedure. A 99.99996% reduction in Colony Forming Units (CFU) is observed for this sample. The silver stearate powder used in this example has a particle size of less than 25 μm. The clear coat powder used in this example has a particle size of less than 25 μm.

Example 2

Composition 2. Cupric stearate powder is added to a clear coat powder coat material supplied by The Finishing Company, Addison, Ill. The cupric stearate powder and clear coat powder are then mixed vigorously to disperse the cupric stearate powder in the clear coat powder and to form a powder blend. The powder blend is 2.5% cupric stearate and 97.5% clear coat powder by volume. An approximately 5 ml sample of this powder blend is placed in an aluminum foil dish. The sample is heated at 380° F. for 10 minutes and then removed from the oven to cool. The sample is tested for antimicrobial activity using the JIS Z 2801 test protocol. A 99.99996% reduction in CFU is observed for this sample. The cupric stearate powder used in this example has a particle size of less than 25 μm. The clear coat powder used in this example has a particle size of less than 25 μm.

Example 3

Composition 3. Cupric stearate powder and silver stearate powder are added to a clear coat powder coat material of supplied by The Finishing Company, Addison, Ill. The cupric stearate powder and clear coat powder are then mixed vigorously to disperse the cupric stearate powder and silver stearate powder in the clear coat powder and to form a powder blend. The powder blend is 1% cupric stearate, 1% silver stearate and 98% clear coat powder by volume. The powder blend is deposited via an electrostatic powder coat process onto stainless steel test coupons to form a sample. The sample is tested for antimicrobial activity using the JIS Z 2801 test protocol. A 99.99994% reduction in CFU is observed for this sample. The cupric stearate powder used in this example has a particle size of less than 25 µm. The silver stearate powder used in this example has a particle size of less than 25 µm. The clear coat powder used in this example has a particle size of less than 25 µm.

Example 4

Composition 4. Cupric acetate powder supplied by Sigma-Aldrich, St. Louis. Mo. is added to a clear coat powder coat material supplied by The Finishing Company, Addison, Ill. The cupric acetate powder and clear coat powder are then mixed vigorously to disperse the cupric acetate powder in the clear coat powder and to form a powder blend. The powder blend is 2.8% cupric acetate and 97.2% clear coat powder by volume. An approximately 5 ml sample of this powder blend is placed in an aluminum foil dish. The sample is heated at 380° F. for 10 minutes and then removed from the oven to cool. The sample is tested for antimicrobial activity using the JIS Z 2801 test protocol. A 99.99831% reduction in CFU is observed for this sample. The cupric acetate powder used in this example has a particle size of less than 25 µm. The clear coat powder used in this example has a particle size of less than 25 µm.

Example 5

Composition 5. Silver acetate powder supplied by Sigma-Aldrich, St Louis, Mo. is added to a clear coat powder coat material supplied by The Finishing Company, Addison, Ill. The silver acetate powder and clear coat powder are then mixed vigorously to disperse the silver acetate powder in the clear coat powder and to form a powder blend. The powder blend is 2.8% silver acetate and 97.2% clear coat powder by volume. An approximately 5 ml sample of this powder blend is placed in an aluminum foil dish. The sample is heated at 380° F. for 10 minutes and then removed from the oven to cool. The sample is tested for antimicrobial activity using the JIS Z 2801 test protocol. A 99.99831% reduction in Colony Forming Units (CFU) is observed for this sample. The silver acetate powder used in this example has a particle size of less than 25 µm. The clear coat powder used in this example has a particle size of less than 25 µm.

The thermoset powder coatings of Examples 1, 2, 3, 4 and 5, i.e., Compositions 1, 2, 3, 4 and 5, demonstrate that cupric stearate, silver stearate and mixtures of cupric stearate and silver stearate are compatible with thermoset powder coatings and provide antimicrobial properties to the thermoset powder coating.

Example 6

Composition 6. Silver stearate powder and cupric stearate powder were added to commercial polypropylene pellets (supplied by a commercial manufacturer). A 2% by volume powder blend was produced (1% silver stearate and 1% cupric stearate) with about 1 pound of polypropylene pellets. The samples were thermal injection molded into disks by a commercial manufacturer following standard industry processes for polypropylene. The sample is tested for antimicrobial activity using the JIS Z 2801 test protocol and 99.99989% reduction in Colony Forming Units (CFU) is observed for this sample. The silver stearate powder used in this example had a particle size of less than about 25 µm. The cupric stearate powder used in this example had a particle size of less than about 25 µm. The polypropylene pellet size was about 4 mm.

Example 7

Composition 7. Silver stearate powder and cupric stearate powder were added to commercial polypropylene pellets (supplied a commercial manufacturer). A 0.2% by volume powder blend was produced (0.1% silver stearate and 0.1% cupric stearate) with about 1 pound of polypropylene pellets. The samples were thermal injection molded into disks by a commercial manufacturer following standard industry processes for polypropylene. The sample is tested for antimicrobial activity using the JIS Z 2801 test protocol and 99.76966% reduction in Colony Forming Units (CFU) is observed for this sample. The silver stearate powder used in this example had a particle size of less than about 25 µm. The cupric stearate powder used in this example had a particle size of less than about 25 µm. The polypropylene pellet size was about 4 mm. This demonstrates that the volume fraction of additive can produce different efficacy levels in the final product. This enables optimization for a variety of product attributes e.g. cost, efficacy, processing, and performance via permutations of the metal and organic components.

The injection molded products of Examples 6 and 7, i.e., Compositions 6 and 7, demonstrate that cupric stearate and silver stearate mixtures are compatible with injection molded polymer products and provide antimicrobial properties to the injection molded polymer product.

Example 8

Composition 8. Cupric stearate powder and silver stearate powder was added to 2-part commercial polyurethane (Envirotex Lite Pour-on High Gloss Finish Polyurethane, Environmental Technology, Inc, Fields Landing, Calif. 95537) at room temperature. A 1.1% by volume powder blend was produced (1% cupric stearate and 0.1% silver stearate) with the liquid polyurethane. The polyurethane was cast over a test coupon per the manufacturer's directions. The sample is tested for antimicrobial activity using the JIS Z 2801 test protocol and 99.99997% reduction in Colony Forming Units (CFU) is observed for this sample.

Example 9

Composition 9. Cupric stearate powder and silver stearate powder was added to 1-part commercial water-based polyurethane (Hanson Group, Atlanta Ga.). A 1.1% by volume powder blend was produced (1% cupric stearate and 0.1% silver stearate) with the liquid water-based polyurethane at room temperature. The polyurethane was spray deposited over a test coupon per the manufacturer's standard operating procedures. The sample is tested for antimicrobial activity using the JIS Z 2801 test protocol and 99.99982% reduction in Colony Forming Units (CFU) is observed for this sample.

The polyurethane coatings of Examples 8 and 9, i.e., Compositions 8 and 9, demonstrate that cupric stearate and silver stearate mixtures are compatible with polyurethane and provide antimicrobial properties to a polyurethane coating. Composition 9 also demonstrates that a polyurethane including the antimicrobial organometallic additives cupric stearate and silver stearate may be deposited as a coating on a substrate via spray deposition techniques, the spray deposition techniques used in Example 9 being different that the electrostatic-based powder coat process technique described above in Example 3.

Figure 15:
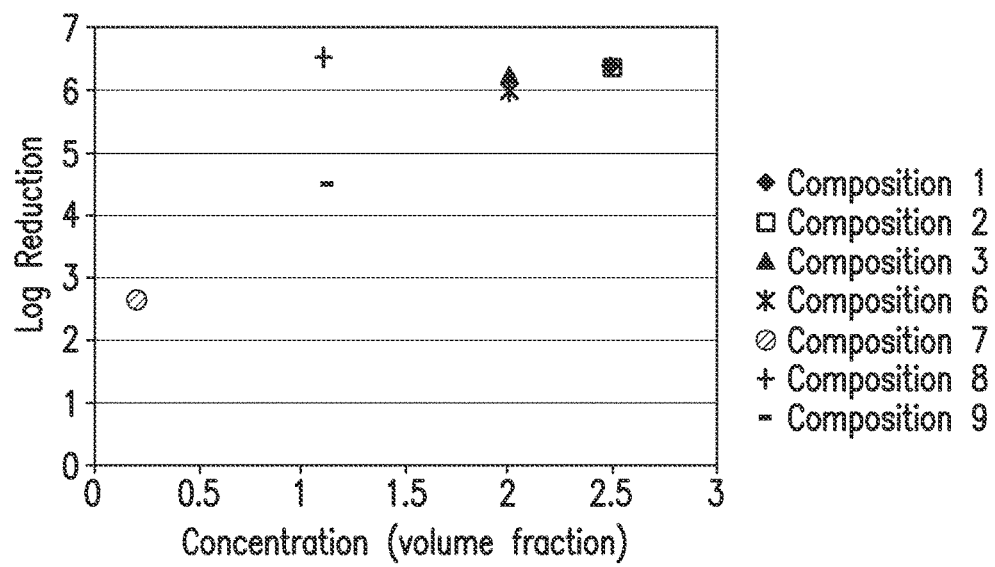
FIG. 15 is a graph of various host polymers containing stearate based organometallic additives showing antimicrobial efficacy performance for various embodiments of the present invention.

This enables optimization of the antimicrobial organometallic additives used for a variety of product attributes e.g. cost, efficacy, processing, and performance via permutations of the metal and organic components. The results for various embodiments of the present invention employing organometallic stearate additives in host polymers are summarized in FIG. 15 which shows various host polymers containing stearate based organometallic additives showing antimicrobial efficacy performance. As seen in FIG. 15, there is a "plateau region" where efficacy is not strongly affected by changes in the volume fraction of organometallic stearate additive(s) added to the host polymer. In addition to concentration measured by volume fraction, concentration can also be measured by atom fraction or molecular fraction. At lower volume fraction concentrations, the efficacy increases smoothly with the concentration. This curve, and resulting curve fit parameters, enable optimization in the amount of organometallic stearate additive used in compositions of the present invention. Note in FIG. 15 that the Compositions 1 and 2 overlap each other.

Figure 16:
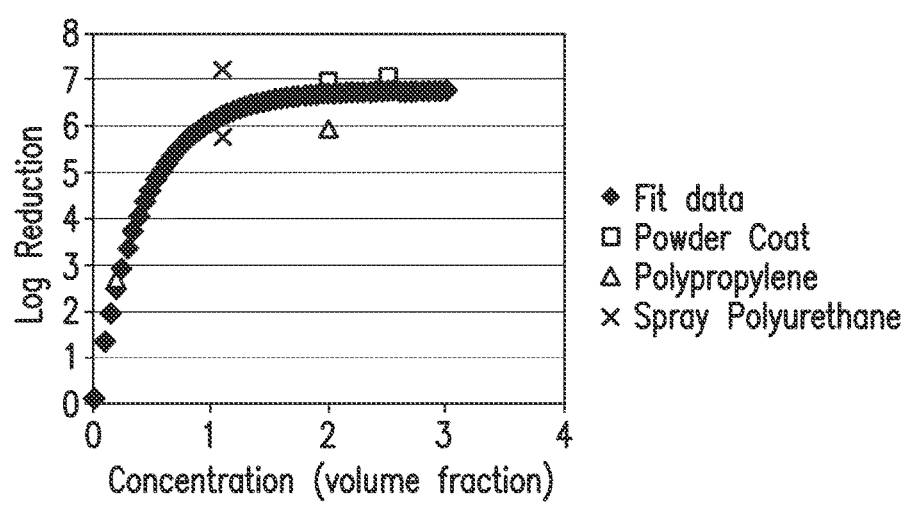
FIG. 16 is a graph showing a curve fit to the data set of FIG. 15.

FIG. 16 shows the data depicted in FIG. 15 that has been fit with a curve defined by Equation 1 below:

$$Y=b+(a-b)/(1+10^{(X-c)}) \quad \text{(Equation 1)}$$

where Y is the Log Reduction result derived from the JIS Z 2081 test protocol, X is the concentration of the antimicrobial organometallic additive and parameters $a=-2.306\times10^6$, $b=6.769$ and $c=-5.530$. Equation 1 is a type of dose reduction model, and the fitted data has a chi-square value of 1.163 and an R-square value of 0.975, indicating a reasonable fit to the data. Other equations or systems of equations can also be used, for example the sum of a linear function to approximate the slowly varying concentration "plateau region" plus a polynomial function to approximate the smoothly increasing section of the data set prior to the "plateau region."

FIG. 16 shows the efficacy performance data grouped by various host polymers, i.e., powder coat material, polypropylene, and polyurethane, with one or more antimicrobial organometallic stearate additives. There is a plateau where efficacy is not affected by changes in the volume fraction of antimicrobial organometallic additive(s) added to the host polymer. At lower volume fraction concentrations, the efficacy varies smoothly with the concentration. This curve, and resulting curve fit parameters, enables optimization of cost and efficacy, via permutations in the concentrations of the antimicrobial organometallic additives.

Figure 17:
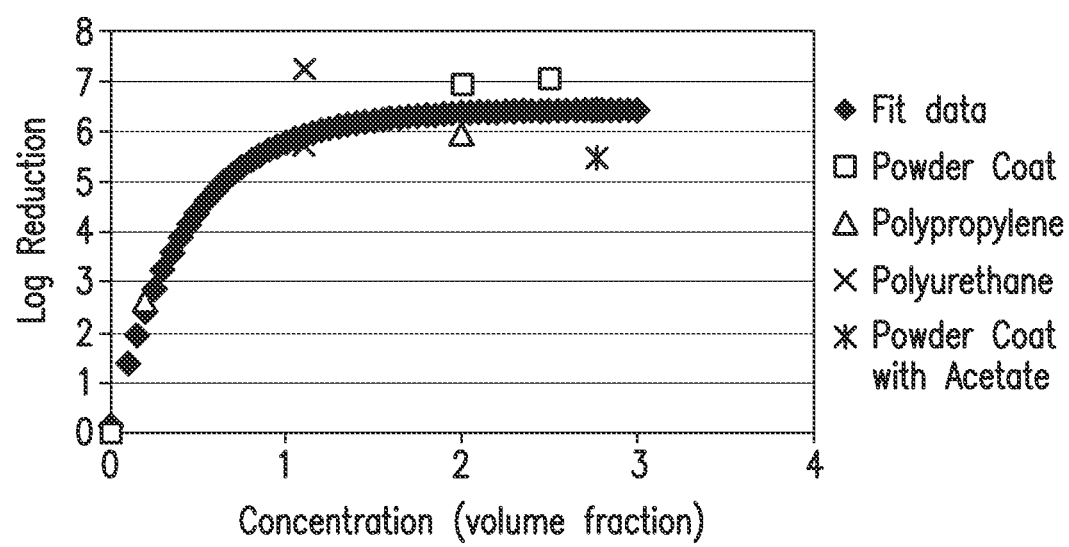
FIG. 17 is a graph of the stearate chemistry data set of FIG. 16 with the inclusion of data where the antimicrobial organometallic additive is an acetate.

FIG. 17 is a graph of the stearate chemistry data set of FIG. 16 with the inclusion of data where the antimicrobial organometallic additive is an acetate (Compositions 4 and 5).

Similar to FIG. 16, FIG. 17 has a "plateau region" where efficacy is not strongly affected by changes in the volume fraction of antimicrobial organometallic additive(s) added to the host polymer. At lower volume fraction concentrations, the efficacy increases smoothly with the concentration. This curve, and resulting curve fit parameters, enables optimization of cost and efficacy, via permutations in the concentrations of the antimicrobial organometallic additive(s).

The data in FIG. 17 has been fit with the curve defined by Equation 1 above, where Y is the Log Reduction result derived from the JIS Z 2081 test protocol, X is the concentration of the antimicrobial organometallic additive(s) and parameters $a=-5.759E6$, $b=6.433$ and $c=-5.957$. In this case, the fitted data has a CHI-Square value of 3.614 and an R-square value of 0.922, indicating a still reasonable fit to the data. Other equations or systems of equations can also be used, for example the sum of a linear function to approximate the slowly varying concentration "plateau region" plus a polynomial function to approximate the smoothly increasing section of the data set prior to the "plateau region".

Example 10

Composition 10. Cupric stearate powder and silver stearate powder was added to commercial food grade paraffin wax (Gulf Wax Household Paraffin Wax, distributed by Royal Oak Enterprises, LLC, Roswell, Ga. 30076). A 1.1% by volume powder blend was produced (1% cupric stearate and 0.1% silver stearate) by adding the powders to molten wax at a temperature of about 90° C. The molten wax mixture was deposited over a paper substrate (butcher paper). The sample coated the substrate in a uniform manner. Immersion in water for 48 hours did not cause the paper substrate of wax-coated paper to wet. It is expected that this sample will have antimicrobial activity similar to the antimicrobial activity of the samples described above in Examples 1, 2, 3, 4, 5, 6, 7, 8 and 9.

All documents, patents, journal articles and other materials cited in the present application are incorporated herein by reference.

Having described a particular embodiment of the present invention, it will be apparent that modifications and variations are possible without departing from the scope of the invention as defined in the appended claims. Furthermore, it should be appreciated that all examples provided in the present disclosure, while illustrating a particular embodiment of the invention, are provided as non-limiting examples and are, therefore, not to be taken as limiting the various aspects so illustrated.

While the present invention has been disclosed with references to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims and equivalents thereof.

What is claimed is:

1. A product comprising:
    a polymer host matrix comprising a polyurethane, and
    one or more antimicrobial organometallic additives dispersed throughout the polymer host matrix,
    wherein the one or more antimicrobial organometallic additives are dispersed throughout the polymer host matrix by mixing the one or more antimicrobial organometallic additives in a powder form with a liquid polyurethane, and
    wherein the one or more antimicrobial organometallic additives comprise one or both members of the group consisting of cupric stearate and zinc stearate.

2. The product of claim 1, wherein the one or more antimicrobial organometallic additives comprise cupric stearate.

3. The product of claim 1, wherein the one or more antimicrobial organometallic additives comprise zinc stearate.

4. The product of claim 2, wherein the one or more antimicrobial organometallic additives comprise a mixture of cupric stearate with one or more members of the group consisting of the following antimicrobial organometallic additives: silver stearate and zinc stearate.

5. The product of claim 2, wherein the product has a degree of antimicrobial activity of 99% or greater.

6. The product of claim 5, wherein the one or more antimicrobial organometallic additives together comprise no more than about 3% by volume of the total volume of the polymer host matrix and the one or more antimicrobial organometallic additives.

7. The product of claim 2, wherein product comprises a coating and a substrate, and wherein the polymer host matrix is at least part of the coating.

8. A method of making the product of claim 1, wherein the method comprises the following step:
   (a) mixing one or more antimicrobial organometallic additives in powder form with a liquid polyurethane at room temperature to form the product.

9. The method of claim 8, wherein the one or more antimicrobial organometallic additives comprise cupric stearate.

10. The method of claim 8, wherein the one or more antimicrobial organometallic additives comprise zinc stearate.

11. The method of claim 8, wherein the one or more antimicrobial organometallic additives comprise a mixture of two or more members of the group consisting of the following antimicrobial organometallic additives: silver stearate, cupric stearate and zinc stearate.

12. The method of claim 8, wherein the product has a degree of antimicrobial activity of 99% or greater.

13. The method of claim 12, wherein the one or more antimicrobial organometallic additives together comprise no more than about 3% by volume of the total volume of the polymer host matrix and the one or more antimicrobial organometallic additives.

14. The method of claim 8, wherein the method comprises the following step:
   (b) applying the product to a substrate to form a coating on the substrate.

15. A product comprising:
   a polymer host matrix comprising a polyurethane, and
   two or more antimicrobial organometallic additives dispersed throughout the polymer host matrix,
   wherein the two or more antimicrobial organometallic additives are dispersed throughout the polymer host matrix by mixing the two or more antimicrobial organometallic additives in a powder form with a liquid polyurethane, and
   wherein the one or more antimicrobial organometallic additives comprise a mixture of two or more members of the group consisting of the following antimicrobial organometallic additives: silver stearate, cupric stearate and zinc stearate.

16. The product of claim 15, wherein the product has a degree of antimicrobial activity of 99% or greater, and wherein the one or more antimicrobial organometallic additives together comprise no more than about 3% by volume of the total volume of the polymer host matrix and the one or more antimicrobial organometallic additives together.

17. The product of claim 3, wherein the one or more antimicrobial organometallic additives comprise a mixture of zinc stearate with one or more members of the group consisting of the following antimicrobial organometallic additives: silver stearate and cupric stearate.

18. The product of claim 3, wherein the product has a degree of antimicrobial activity of 99% or greater.

19. The product of claim 18, wherein the one or more antimicrobial organometallic additives together comprise no more than about 3% by volume of the total volume of the polymer host matrix and the one or more antimicrobial organometallic additives.

20. The product of claim 3, wherein product comprises a coating and a substrate, and wherein the polymer host matrix is at least part of the coating.

\* \* \* \* \*